(12) United States Patent
Zhang et al.

(10) Patent No.: US 11,458,005 B2
(45) Date of Patent: Oct. 4, 2022

(54) SELF-CENTERING INFERIOR VENA CAVA FILTER

(71) Applicant: Hangzhou Endonom Medtech Co., Ltd, Zhejiang (CN)

(72) Inventors: Tingchao Zhang, Zhejiang (CN); Yang Li, Zhejiang (CN)

(73) Assignee: HANGZHOU WEI QIANG MEDICAL TECHNOLOGY CO., LTD., Hangzhou (CN)

( * ) Notice: Subject to any disclaimer, the term of this patent is extended or adjusted under 35 U.S.C. 154(b) by 437 days.

(21) Appl. No.: 16/220,411

(22) Filed: Dec. 14, 2018

(65) Prior Publication Data

US 2019/0117368 A1 Apr. 25, 2019

Related U.S. Application Data

(63) Continuation of application No. PCT/CN2018/079700, filed on Mar. 21, 2018.

(30) Foreign Application Priority Data

Apr. 11, 2017 (CN) .......................... 201720377894.5

(51) Int. Cl.
*A61F 2/01* (2006.01)
*A61F 2/848* (2013.01)

(52) U.S. Cl.
CPC .......... *A61F 2/0103* (2020.05); *A61F 2/0105* (2020.05); *A61F 2002/016* (2013.01);
(Continued)

(58) Field of Classification Search
CPC ........ A61F 2/01; A61F 2/0103; A61F 2/0105; A61F 2/012; A61F 2002/016; A61F 2/0108
See application file for complete search history.

(56) References Cited

U.S. PATENT DOCUMENTS

| 5,669,933 A | 9/1997 | Simon et al. |
| 6,258,026 B1 | 7/2001 | Ravenscroft et al. |

(Continued)

FOREIGN PATENT DOCUMENTS

| CN | 102470028 A | 5/2012 |
| CN | 102811679 A | 12/2012 |

(Continued)

OTHER PUBLICATIONS

International search report issued in corresponding international application No. PCT/CN2018/079700 dated Jun. 19, 2018.

(Continued)

*Primary Examiner* — Elizabeth Houston
*Assistant Examiner* — Lindsey Bachman
(74) *Attorney, Agent, or Firm* — Hauptman Ham, LLP

(57) ABSTRACT

The self-centering inferior vena cava filter is provided, which includes a filter portion, a support portion, and a retrieval portion. The filter portion is configured to filter thrombi and includes at least two layers of filter members extending along a central axis of the self-centering inferior vena cava filter, the at least two layers of filter members are adjacent to each other and staggered around the central axis. The support portion is configured to prevent the self-centering inferior vena cava filter from tilting, and extends outwardly radially from a center point of the support portion in a direction close to the filter portion and then curls inwardly radially in a direction away from the filter portion, and is supported on a blood vessel wall by point contact. The retrieval portion is connected with at least one of the filter portion and the support portion.

20 Claims, 5 Drawing Sheets

(52) U.S. Cl.
CPC . *A61F 2002/8483* (2013.01); *A61F 2230/005* (2013.01); *A61F 2230/0067* (2013.01); *A61F 2230/0073* (2013.01); *A61F 2230/0093* (2013.01)

(56) References Cited

U.S. PATENT DOCUMENTS

| | | | | |
|---|---|---|---|---|
| 7,972,353 | B2* | 7/2011 | Hendriksen | A61F 2/01 606/200 |
| 2005/0055045 | A1* | 3/2005 | DeVries | A61F 2/01 606/200 |
| 2007/0173885 | A1* | 7/2007 | Cartier | A61F 2/01 606/200 |
| 2008/0228209 | A1* | 9/2008 | DeMello | A61B 17/32056 606/159 |
| 2011/0137335 | A1* | 6/2011 | Hallisey | A61F 2/012 606/200 |
| 2013/0035714 | A1 | 2/2013 | Snow | |
| 2014/0277080 | A1* | 9/2014 | Johnsen | A61F 2/012 606/200 |

FOREIGN PATENT DOCUMENTS

| | | |
|---|---|---|
| CN | 203841850 U | 9/2014 |
| CN | 104825247 A | 8/2015 |
| CN | 205339216 U | 6/2016 |
| CN | 105943197 A | 9/2016 |
| CN | 107007377 A | 8/2017 |
| CN | 207821947 U | 9/2018 |
| EP | 1 974 692 * | 1/2008 |
| EP | 1974692 A1 | 10/2008 |
| GB | 2531019 A | 4/2016 |
| WO | 95/09567 A1 | 4/1995 |
| WO | 2011/055079 A1 | 5/2011 |

OTHER PUBLICATIONS

Chinese Office Action issued in corresponding Chinese Application No. 201880002404.0, dated Mar. 30, 2020, pp. 1-18, The State Intellectual Property Office of People's Republic of China, Beijing, China.

Examination Report issued in corresponding EP Application No. EP18784333.9, dated Feb. 24, 2021.

* cited by examiner

SELF-CENTERING INFERIOR VENA CAVA FILTER

CROSS-REFERENCE TO RELATED APPLICATION(S)

This application is a continuation of PCT/CN2018/079700, filed on Mar. 21, 2018, which claims priority to Chinese Patent Application No. 201720377894.5, filed on Apr. 11, 2017, the disclosure of which are hereby incorporated by reference in their entirety.

TECHNICAL FIELD

The present disclosure belongs to the technical field of medical devices, and relates to an inferior vena cava filter, and particularly relates to a self-centering inferior vena cava filter.

BACKGROUND

Pulmonary embolism (PE) is a common health problem and becomes an important factor leading to death in all age groups. Most pulmonary embolism result from deep vein thrombosis (DVT) of the lower extremities or the pelvis. Blood clots of the deep vein thrombosis may flow back into the heart through the veins and then into the lung, thereby causing pulmonary infarction due to loss of a portion supply of blood and oxygen to the lung.

An overall structure of an inferior vena cava filter in the related art is generally formed in a cone shape. The inferior vena cava filter in a cone shape has a poor self-centering performance and is easy to tilt after being implanted into the inferior vena cava. When the inferior vena cava filter is tilted, a retrieval hook of the inferior vena cava filter may be closely attached to the vessel wall. In the process of retrieving the inferior vena cava filter, a retrieval device can not capture the retrieval hook smoothly, which makes it difficult to retrieve the inferior vena cava filter successfully, thereby increasing the operation time duration as well as the suffering of the patient, and even leading to a failure of retrieval operation of the inferior vena cava filter.

SUMMARY

The technical problem to be solved by the present disclosure is the above-mentioned shortcomings in the related art. The present disclosure provides a self-centering inferior vena cava filter with good self-centering performance to prevent a retrieval hook of a retrieval portion from being attached to a blood vessel wall.

The technical solutions adopted by the present disclosure to solve the technical problem are described as follows.

A self-centering inferior vena cava filter is provided, which includes a filter portion, a support portion, and a retrieval portion.

The filter portion is configured to filter thrombi and includes at least two layers of filter members extending along a central axis of the self-centering inferior vena cava filter, the at least two layers of filter members are adjacent to each other and staggered around the central axis.

The support portion is configured to prevent the self-centering inferior vena cava filter from tilting, and extends outwardly radially from a center point of the support portion in a direction close to towards the filter portion and then curls inwardly radially in a direction away from the filter portion, and is supported on a blood vessel wall by point contact.

The retrieval portion is connected with at least one of the filter portion and the support portion.

In one implementation of the present disclosure, each of the at least two layers of the filter members includes a plurality of struts extending outwardly radially from a center point of the filter members, the plurality of struts of the filter members adjacent to each other are staggered around the central axis, and the plurality of struts of the filter member closest to the support portion are staggered with support struts of the support portion.

In one implementation of the present disclosure, each of the plurality of struts of the filter member closest to the support portion includes at least a first segment, a second segment, and a third segment extending sequentially outwardly radially from the center point of the filter member. The first segment is in a straight-line shape and parallel to the central axis, each of the second segment and the third segment is in a straight-line shape or a curved-line shape and extends gradually outwardly radially. The slope of the third segment is less than that of the second segment, or the radius of curvature of the third segment is greater than that of the second segment. Smooth transitions between the first segment, the second segment, and the third segment are provided.

In one implementation of the present disclosure, the second segment curls radially away from the central axis, and the third segment curls radially toward the central axis.

In one implementation of the present disclosure, the third segment further includes a fourth segment extending outwardly radially, e fourth segment is in a straight-line shape or a curved-line shape. The fourth segment further includes a fifth segment extending parallel to or curling toward the central axis.

In one implementation of the present disclosure, each of the plurality of struts of the filter members other than the filter member closest to the support portion includes at least a first segment, a second segment, and a third segment extending sequentially outwardly radially from the center point of the filter member. The first segment is in a straight-line shape and parallel to the central axis, the second segment is in a curved-line shape and curls outwardly radially, and the third segment is in a straight-line shape or a curved-line shape and extends gradually outwardly radially.

In one implementation of the present disclosure, the support portion includes at least three support struts extending outwardly radially from the center point of the support portion and being symmetric about the central axis. An end of the support strut or a tangent of the end of the support strut, and the central axis define an angle therebetween, and the angle is greater than or equal to 180 degrees. A maximum outer diameter of the support portion is substantially coincident with an inner diameter of the blood vessel such that the support struts are supported on the blood vessel wall by point contact.

In one implementation of the present disclosure, each of the support struts includes a first support segment and a second support segment extending sequentially outwardly radially from the center point of the support portion.

The first support segment or a tangent of each point of the first support segment, and the central axis define an angle therebetween ranging from zero to 90 degrees.

The second support segment or a tangent of each point of the second support segment, and the central axis define an angle therebetween greater than 90 degrees.

An end of the second support segment or a tangent of the end of the second support segment, and the central axis define an angle therebetween greater than or equal to 180 degrees.

The second support segment or a tangent of each point of the second support segment, and the first support segment define an angle greater than or equal to 90 degrees.

In one implementation of the present disclosure, the second support segment includes a first sub-segment, a second sub-segment, and a third sub-segment. The radius of curvature of the second sub-segment is less than that of the first sub-segment. The second sub-segment and the central axis define an angle therebetween, the angle changes from being greater than or equal to 90 degrees and less than 180 degrees to be greater than or equal to 180 degrees.

Alternatively, the second sub-segment is in a curved-line shape or a fold-line shape with a C-shaped or V-shaped opening facing the central axis. Each of the first sub-segment and the third sub-segment is in a straight-line shape or a fold-line shape, and the entire second support segment curls away from or toward the filter members.

In one implementation of the present disclosure, the cross-sectional area of each of the support struts of the support portion is gradually reduced toward the end of the support strut.

In one implementation of the present disclosure, at least one of the support portion and the filter members is provided with anchoring portions.

The support portion extends outwardly radially from the center point of the support portion in a direction towards the filter portion and then curls inwardly radially in a direction away from the filter portion, and is supported on the blood vessel wall by point contact, such that the self-centering inferior vena cava filter is of good self-centering performance to prevent the self-centering inferior vena cava filter from tilting. The support portion contacts with the blood vessel wall at a relatively small contact area, thereby reducing the climbing and covering of the vascular intima and facilitating the retrieval of the self-centering inferior vena cava filter. As a result, the operation time duration can be shortened, the service life of the self-centering inferior vena cava filter can be increased, and the timing of retrieving the self-centering inferior vena cava filter can be delayed.

The filter portion includes at least two layers of filter members extending along a central axis of the self-centering inferior vena cava filter, the at least two layers of filter members are adjacent to each other and staggered around the central axis, which can enhance filtering effectiveness of the filter portion.

BRIEF DESCRIPTION OF THE DRAWINGS

The present disclosure can be further illustrated in conjunction with the accompanying drawings and embodiments.

DETAILED DESCRIPTION

Figure 1:
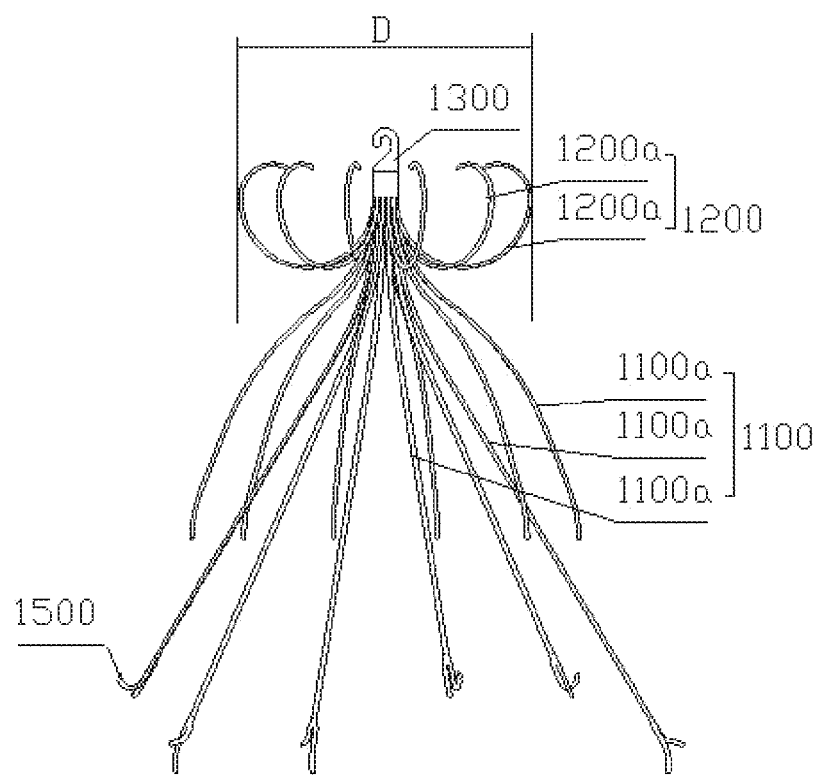
FIG. 1 is a schematic structural view of a self-centering inferior vena cava filter according to a first embodiment of the present disclosure.
Figure 2:
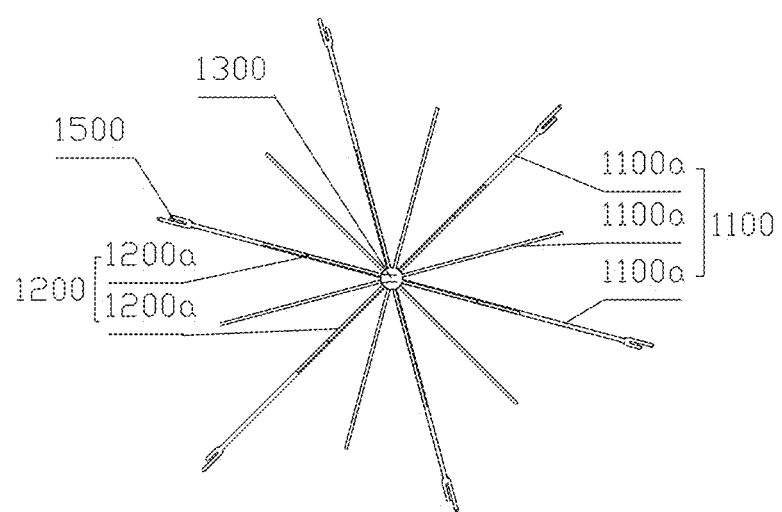
FIG. 2 is a top view of the self-centering inferior vena cava filter illustrated in FIG. 1.

To illustrate objectives, technical solutions, and advantageous effects of the disclosure more clearly, the specific embodiments of the present disclosure will be described in detail herein with reference to accompanying drawing.

The orientations in embodiments of the present disclosure are defined as follows. A self-centering inferior vena cava filter with a central axis is provided. The central axis also refers to a central axis of a first support portion, a central axis of a filter portion, and a central axis of a second support portion.

In a first embodiment, as illustrated in FIGS. 1-7, a self-centering inferior vena cava filter is provided. The self-centering inferior vena cava filter includes a filter portion 1100, a support portion 1200, and a retrieval portion 1300. The filter portion 1100 is configured to filter thrombi and includes at least two layers of filter members extending along a central axis of the self-centering inferior vena cava filter, the at least two layers of filter members are adjacent to each other and staggered around the central axis. The support portion 1200 is configured to prevent the self-centering inferior vena cava filter from tilting and extends outwardly radially from a center point of the support portion 1200 in a direction towards the filter portion and then curls inwardly radially in a direction away from the filter portion. The support portion 1200 is supported on a blood vessel wall by point contact. The retrieval portion 1300 is connected with at least one of the filter portion 1100 and the support portion 1200. The point contact causes the overall filter has a self-centering performance in the inferior vena cava. The retrieval portion 1300 includes a retrieval hook substantially located on or close to the central axis, such that the retrieval hook can be located away from the blood vessel wall. In addition, the self-centering inferior vena cava filter is prevented from tilting to avoid that the retrieval portion 1300 is attached to the blood vessel wall.

In one implementation, the self-centering inferior vena cava filter includes at least the retrieval portion 1300, the support portion 1200, and the filter portion 1100. The filter portion 1100 includes at least two layers of filter members. The number of layers of the filter members can be set according to the practice needs, and generally the filter members include at least two layers. Each of the at least two layers of the filter members includes multiple struts 1100*a* extending outwardly radially from a center point of the filter members, the multiple struts 1100*a* of the filter members adjacent to each other are staggered around the central axis, and the multiple struts 1100*a* of the filter member closest to the support portion 1200 are staggered with support struts 1200a of the support portion 1200. The at least two layers of filter members are attached together and connected with the support portion 1200. The center point of the support portion 1200 and the center point of the filter portion 1100 are located on the same line (that is, the central axis of the self-centering inferior vena cava filter), and preferably the center point of the filter portion 1100 coincides with the center point of the support portion 1200. The at least two layers of filter members includes a first layer filter member, a second layer filter member, and the other layer filer members. The first layer filter member then the second layer filter member and so on until the last layer filter member are sequentially disposed away from the support portion 1200. The struts 1100a of the first layer filter member closest to the support portion 1200 are staggered with the support struts 1200a of the support portion 1200 around the central axis. In one implementation, projections of filter members of odd-numbered layers on a plane perpendicular to the central axis do not overlap that of filter members of even-numbered layers. The center point of the first layer filter member and the center point of the second layer filter member coincide, that is, the center point of the filter portion 1100.

The struts 1100a of the filter member of each layer extend outwardly radially from the center point of the filter member. All of the struts 1100a are arranged symmetrically about the central axis. The filter member of each layer includes at least three struts 1100a. As illustrated in FIG. 1, the filter portion includes three layers of filter members. The first layer filter member includes six struts 1100a. The second layer filter member and the last layer filter member both include three struts 1100a. The struts 1100a of each layer are arranged symmetrically about the central axis.

Figure 3:
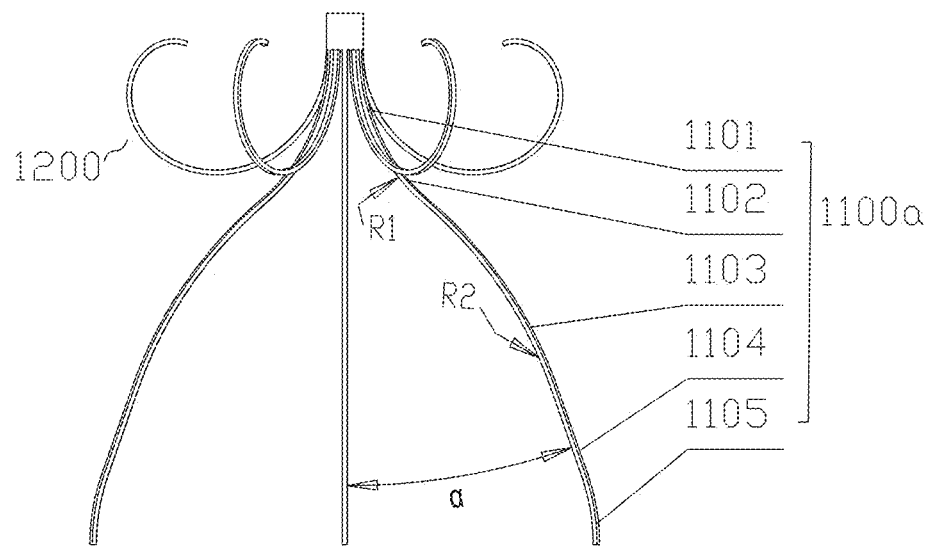
FIG. 3 is a schematic structural view illustrating a support portion and a first layer filter member according to the first embodiment of the present disclosure.

As illustrated in FIG. 3, each of the multiple struts 1100a of the filter member closest to the support portion 1200 includes at least a first segment 1101, a second segment 1102, and a third segment 1103 extending sequentially outwardly radially from the center point of the filter member. The first segment 1101 is in a straight-line shape and substantially parallel to the central axis. The length of the first segment 1101 can be set depending on the practical needs. In one alternative implementation, the length of the first segment 1101 is ranged from zero to 5 mm. That is, the length of the first segment 1101 is not greater than 5 mm. Alternatively, the strut 1100a may be provided without the first segment 1101. Each of the second segment 1102 and the third segment 1103 is in a straight-line shape or a curved-line shape and extends gradually outwardly radially. The slope of the third segment 1103 is less than that of the second segment 1102. Alternatively, the radius of curvature of the third segment 1103 is greater than that of the second segment 1102. That is, the extent to which the third segment 1103 extends outwardly radially is less than that of the second segment 1102. Smooth transitions between the first segment 1101, the second segment 1102, and the third segment 1103 are provided. In the first embodiment, the second segment 1102 is in a curved-line shape. The second segment 1102 curls away from the central axis (that is, curls outwardly radially), and in this case, the second segment 1102 has a radius of curvature R1 ranging from 8 mm to 16 mm. The third segment 1103 may also be in a curved-line shape. The third segment 1103 curls toward the central axis. The third segment 1103 has a radius of curvature R2 ranging from 18 mm to 27 mm. In this embodiment, a curved-line segment with a larger radius of curvature is adopted, thereby reducing stress concentration at a center portion. In the blood vessels with smaller diameters, the curved-line segment can reduce the risk of breakage and entanglement of the struts 1100a.

In an alternative implementation, the third segment 1103 further includes a fourth segment 1104 extending outwardly radially, the fourth segment 1104 is in a straight-line shape or a curved-line shape. In the first embodiment, the fourth segment 1104 is in a straight-line shape. The fourth segment 1104 and the central axis define an angle α therebetween ranging from 10 degrees to 30 degrees. The fourth segment 1104 further includes a fifth segment 1105. The fifth segment 1105 is in a straight-line shape or a curved-line shape. When the fifth segment 1105 is in a straight-line shape, the fifth segment 1105 is substantially parallel to the central axis. When the fifth segment 1105 is in a curved-line shape, the fifth segment 1105 curls toward the central axis.

Figure 4:
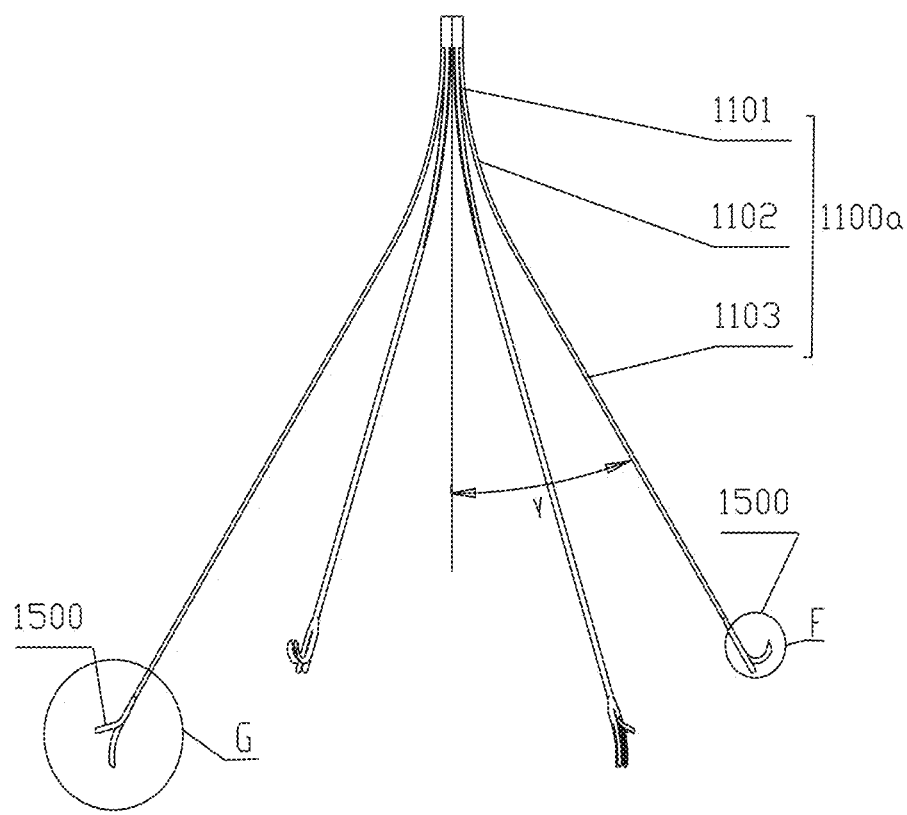
FIG. 4 is a schematic structural view illustrating a filter member according to the first embodiment of the present disclosure.

As illustrated in FIG. 4, each of the multiple struts 1100a of the filter members other than the filter member closest to the support portion 1200 includes at least a first segment 1101, a second segment 1102, and a third segment 1103 extending sequentially outwardly radially from the center point. The first segment is in a straight-line shape and substantially parallel to the central axis. The length of the first segment 1101 ranges from zero to 10 min. The second segment 1102 is in a curved-line shape and curls outwardly radially. In the first embodiment, the second segment 1102 curls away from the central axis of the filter portion 1100 (that is, curls outwardly radially). The second segment 1102 has a radius of curvature R3 ranging from 20 mm to 30 mm. The third segment 1103 is in a straight-line shape or a curved-line shape and extends gradually outwardly radially. In the first embodiment, the third segment 1103 is in a straight-line shape and extends gradually outwardly radially. The third segment 1103 and the central axis define an angle γ therebetween ranging from 15 degrees to 45 degrees.

Figure 7:
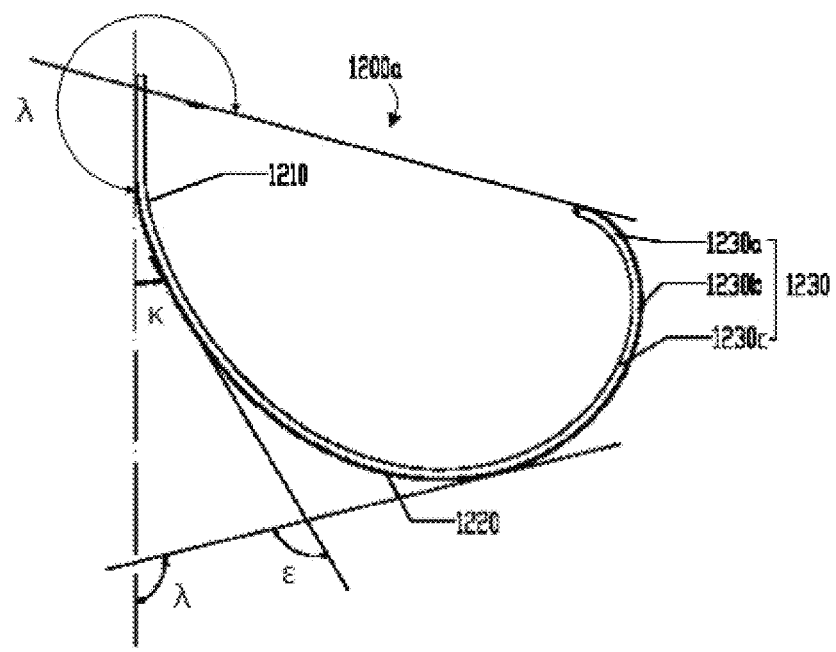
FIG. 7 is a schematic structural view illustrating a support strut according to the first embodiment of the present disclosure.

As illustrated in FIG. 1 and FIG. 7, an end of the support strut 1200a or a tangent of the end of the support strut 1200a, and the central axis of the support portion 1200 define an angel λ therebetween, and the angle λ is greater than or equal to 180 degrees. A maximum outer diameter of the support portion 1200 is substantially coincident with an inner diameter of the blood vessel such that the support struts 1200a are supported on the blood vessel wall by point contact. It should be noted that the maximum outer diameter refers to the diameter of a circle formed by points of the support struts 1200a farthest away from the central axis, that is, the maximum outer diameter is twice a distance between the central axis and a point of the support struts 1200a farthest away from the central axis. During a deploying procedure, the support struts 1200a expand within the blood vessel. When the deploying procedure has been completed, the end of the support strut 1200a or a tangent of the end of the support strut 1200a, and the central axis of the support portion 1200 define the angle λ greater than or equal to 180 degrees, regardless of a structure of the support strut 1200a. Therefore, the end of the support strut 1200a is arranged offset from the blood vessel wall 2000, and at least in parallel with the blood vessel wall 2000, such that the end of the support strut 1200a will not pierce the blood vessel wall 2000.

As illustrated in FIG. 7, the structures and functions of different portions of the support strut 1200a are different. Each of the support struts 1200a mainly includes two parts of a first support segment 1210 and a second support segment 1230. The first support segment 1210 and the second support segment 1230 extend sequentially outwardly radially from the central point. In one implementation, a transition segment 1220 is provided between the first support segment 1210 and the second support segment 1230. The above-mentioned three segments are configured as different structures with different shapes and lengths. The central axis and one of the first support segment 1210 and a tangent of each point of the first support segment 1210 define an angle κ greater than zero and less than 90 degrees. The central axis and one of the second support segment 1230 and a tangent of each point of the second support segment 1230 define an angle λ greater than 90 degrees. In addition, since the end of each of the support struts 1200a is an end of the second support segment 1230, thus an angle κ defined by the central axis and one of the end of the second support segment 1230 and a tangent of the end of the second support segment 1230 is greater than or equal to 180 degrees. Such a structure can ensure that after the support strut 1200a is positioned, the end of the support strut 1200a curls an angle greater than 180 degrees before the support strut 1200a attaches to the blood vessel wall. The ends of the multiple first support segments 1210 are attached together, and the second support segment 1230 is disposed as an end portion of the support strut 1200a.

The first support segment 1210 and one of the second support segment 1230 and a tangent of each point of the second support segment 1230 define an angle c greater than 90 degrees. In one implementation, the first support segment 1210 and one of the second support segment 1230 and a tangent of the second support segment 1230 define an angle ε greater than and equal to 180 degrees, that is, the second support segment 1230 curls in a direction away from the filter portion 1200. The transition segment 1220 is a transition portion between the first support segment 1210 and the second support segment 1230. Therefore, the length and shape of the transition segment 1220 can be determined according to the shapes of the first support segment 1210 and the second support segment 1230, so as to facilitate a smooth transition between the first support segment 1210 and the second support segment 1230, and a corresponding effect of curling is achieved. The first support segment 1210, the second support segment 1230, and the transition segment 1220 may be curved bars, straight bars, fold bars, or a mixed arrangement of at least two bars in the above-described shapes. In one implementation, the first support segment 1210, the second support segment 1230, and the transition segment 1220 are curved bars whose radiuses of curvature continuously changes (that is, the radiuses of curvature gradually reduces).

In this embodiment, the second support segment 1230 of the support strut 1200a includes a first sub-segment 1230a, a second sub-segment 1230b, and a third sub-segment 1230c. In one implementation, the radius of curvature of the second sub-segment 1230b is less than that of the first sub-segment 1230a. The second sub-segment 1230b and the central axis define an angle, and a range of the angle is changing from being greater than or equal to 90 degrees and less than 180 degrees to be greater than or equal to 180 degrees, thereby forming point contact with the blood vessel wall. In another implementation, the second sub-segment 1230b can be in a curved-line shape or a fold-line shape with a C-shaped or V-shaped opening facing the central axis, and forms a point contact with the blood vessel wall. The first sub-segment 1230a and the third sub-segment 1230c can be in a straight-line shape or a fold-line shape, and the entire second support segment 1230 curls away from or toward the filter members.

"Point contact" is a relative concept, meaning that the support strut 1200a contacts blood vessel wall 2000 with a relatively small contact area. Compared with the length and diameter of the support strut 1200a, the contact between the support strut 1200a and the blood vessel wall 2000 can be considered as a kind of point contact.

The support portion 1200 is configured to be in a curved-line shape to maximally prevent the support struts 1200a from attaching to the blood vessel wall 2000 and reduce the climbing and covering of the vascular intima. The self-centering inferior vena cava filter is of good self-centering performance to prevent the filter from tilting and effectively prevent the retrieval hook of the retrieval portion from attaching to the blood vessel wall 2000, thereby facilitating the retrieval of the self-centering inferior vena cava filter. When the filter is required to be retrieved, the retrieval hook of the retrieval portion 1300 can be captured through the jugular vein by a retrieval catheter and a vascular snare, and the entire filter is retrieved into the sheath and taken out of the body.

Figure 5:
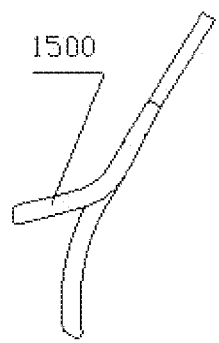
FIGS. 5-6 are schematic structural views illustrating anchoring portions according to the first embodiment of the present disclosure.
Figure 6:
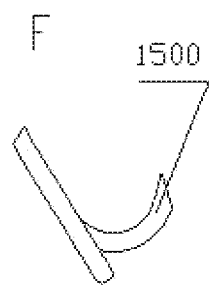

As illustrated in FIG. 1 and FIGS. 4-6, at least one of the end of the support portion 1200 and the end of the filter member is provided with anchoring portions for anchoring in the blood vessel wall 2000. In the first embodiment, ends of the filter members of the filter portion 1100 are provided with anchoring portions 1500. The anchoring portions 1500 can be disposed at the ends of the struts 1100a of each filter member, or at the ends of some of the struts 1100a. In one alternative implementation, the anchoring portions 1500 are disposed at the ends of the struts 1100a whose ends are farthest from the central axis. The ends of the struts 1100a may extend to form the anchoring portions 1500, or branches may be provided close to the ends to form the anchoring portions 1500 with branched structures, thereby avoiding excessively deep penetration of the anchoring portions 1500 into the blood vessel wall 2000. As illustrated in FIGS. 4-6, in the first embodiment, the anchoring portions 1500 are disposed at the ends of the struts 1100a.

As illustrated in FIG. 1, the retrieval portion 1300 is configured to retrieve the self-centering inferior vena cava filter. The retrieval portion 1300 is disposed at the center point of the support portion 1200 (that is, a position where the support struts 1200a are attached together, that is also, the center point of the self-centering inferior vena cava filter). In the first embodiment, the retrieval portion 1300 is provided with a hook (i.e., a retrieval hook) or a hanging loop for retrieving the self-centering inferior vena cava filter into the retrieval catheter.

As illustrated in FIG. 3, each portion of the self-centering inferior vena cava filter is configured as a separate assembly structure. The support struts 1200a of the support portion 1200 and the first layer filter member of the filter portion 1100 are assembled together, and are fixedly connected to the retrieval portion 1300 through a sleeve. The filter members of other layers in FIG. 4 are separately manufactured structures.

In the first embodiment, the filter portion 1100, the support portion 1200, and the retrieval portion 1300 are separately formed and then welded together. The cross-sectional area of each of the support struts 1200a of the support portion 1200 is gradually reduced toward the end thereof.

Figure 8:
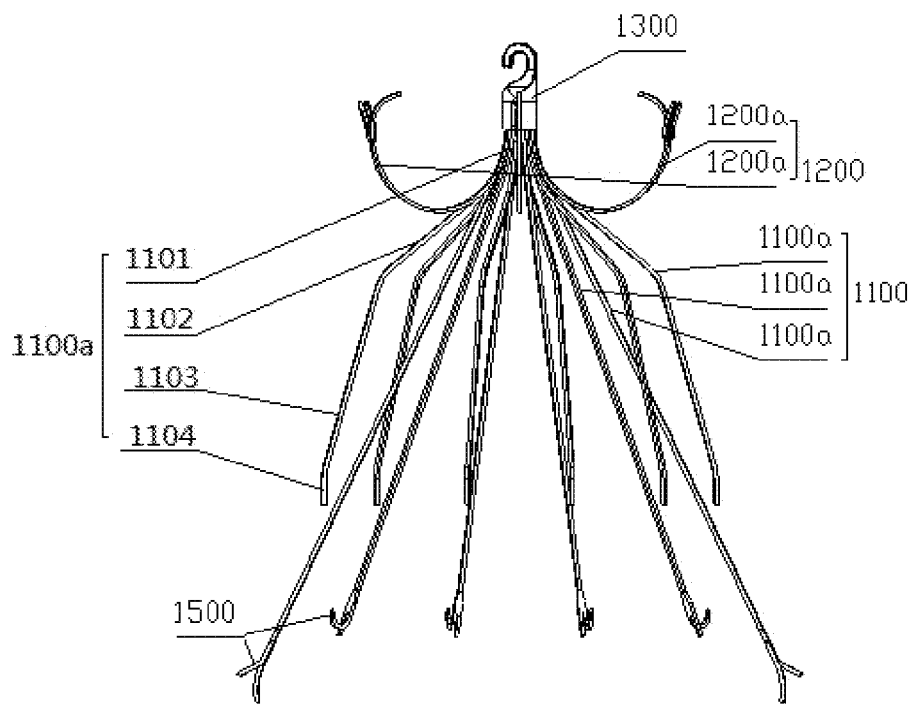
FIG. 8 is a schematic structural view of a self-centering inferior vena cava filter according to a second embodiment of the present disclosure.
Figure 9:
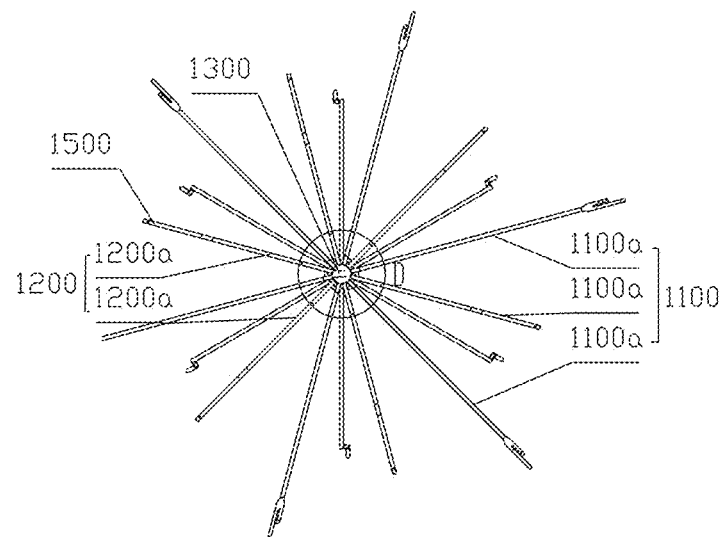
FIG. 9 is a top view of the second embodiment of the present disclosure.

As illustrated in FIG. 8 and FIG. 9, a second embodiment is provided. A basic structure of the filter in the second embodiment is essentially identical with that of the filter in the first embodiment. The difference is that the filter portion 1100 in the second embodiment has a different structure.

Each of the struts 1100a of the first layer filter member closest to the support portion 1200 includes a first segment 1101, a second segment 1102, a third segment 1103, and a fourth segment 1104 disposed sequentially outwardly radially from the center point of the first layer filter member. The first segment 1101, the second segment 1102, the third segment 1103, and the fourth segment 1104 are in straight-line shape, and smooth transitions are provides among the first segment 1101, the second segment 1102, the third segment 11103, and the fourth segment 1104.

The ends of the support struts 1200a of the support portion 1200 may be provided with multiple anchoring portions 1500 to achieve the anchoring of the self-centering interior vena cava filter in the blood vessel wall 2000 and prevent displacement of the filter.

Other structures are the same as those in the first embodiment, which will not be described herein.

Figure 10:
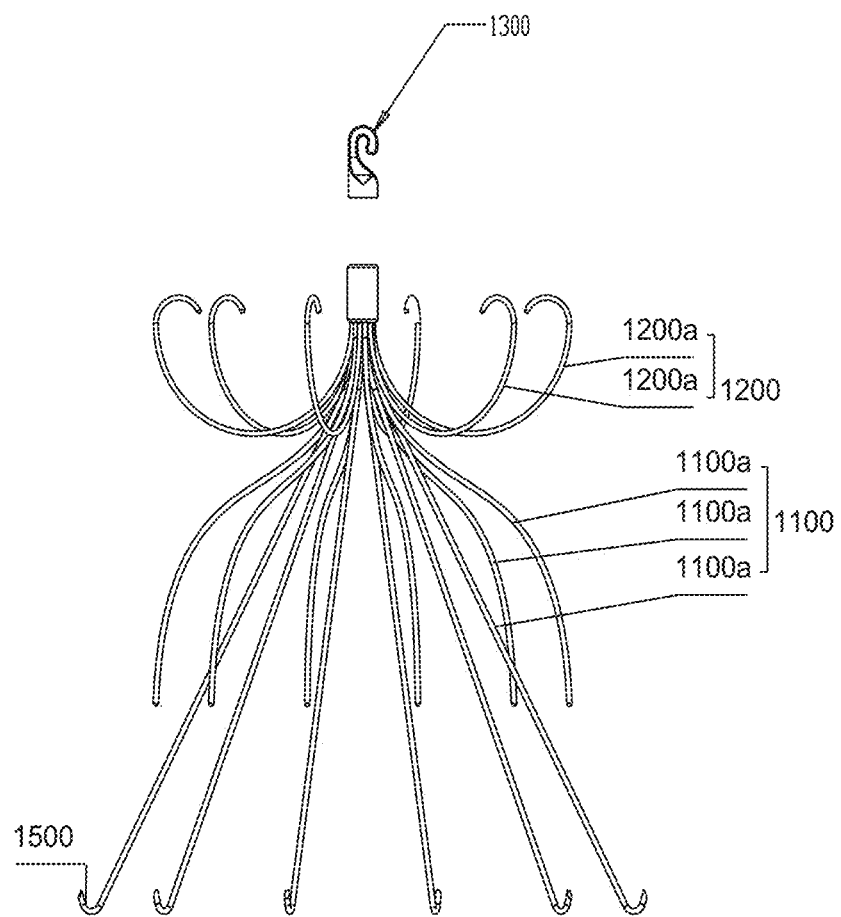
FIG. 10 is a schematic structural view according to a third embodiment of the present disclosure.

As illustrated in FIG. 10, a third embodiment is provided. The overall structure of the filter in the third embodiment is essentially identical with that of the filter in the first embodiment. In the third embodiment, each of the retrieval portion 1300, the support portion 1200, and the filter portion 1100 is configured into wire form, and are fixedly connected with the retrieval portion 1300 through a sleeve.

The support portion 1200 is formed by wire material with a diameter ranging from 0.1 mm to 0.6 mm. The wire material includes, but is not limited to one or more of stainless steel, nickel titanium alloy, cobalt chromium alloy, titanium alloy, and the like. In the third embodiment, the support portion 1200 includes six support struts 1200a made from nickel-titanium wire with a diameter of 0.35 mm. The ends of the support struts 1200a are sleeved on a sleeve 1260 and connected by argon arc welding. And then continuously smooth curved support struts 1200a are formed by a heat setting process through a mold. The struts 1100a are made in the same process as the support struts 1200a.

What is claimed is:

1. A self-centering inferior vena cava filter, comprising:
    a filter portion configured to filter thrombi, comprising at least two layers of filter members extending along a central axis of the self-centering inferior vena cava filter, the at least two layers of filter members being adjacent to each other and staggered around the central axis;
    a support portion configured to prevent the self-centering inferior vena cava filter from tilting, extending outwardly radially from a center point of the support portion in a direction towards the filter portion and then curling inwardly radially in a direction away from the filter portion, and configured to be supported on a blood vessel wall by point contact; and
    a retrieval portion connected with at least one of the filter portion and the support portion;
    wherein
    the support portion comprises support struts,
    for each of the support struts, a free end of the support strut extends from an apex of the support strut inwardly radially towards the filter portion, and
    the apex is farther away from a free end of the filter portion than the free end of the support strut in a direction parallel to the central axis.

2. The self-centering inferior vena cava filter of claim 1, wherein
    each of the at least two layers of the filter members comprises a plurality of struts extending outwardly radially from a center point of the filter members, the plurality of struts of the filter members adjacent to each other being staggered around the central axis, and the plurality of struts of the filter member closest to the support portion being staggered with the support struts of the support portion.

3. The self-centering inferior vena cava filter of claim 2, wherein
    each of the plurality of struts of the filter member closest to the support portion comprises at least a first segment, a second segment, and a third segment extending sequentially radially from the center point of the filter member;
    the first segment is in a straight-line shape and parallel to the central axis, each of the second segment and the third segment is in a straight-line shape or a curved-line shape and extends gradually radially;
    the slope of the third segment is less than that of the second segment, or the radius of curvature of the third segment is greater than that of the second segment; and
    smooth transitions between the first segment, the second segment, and the third segment are provided.

4. The self-centering inferior vena cava filter of claim 3, wherein the second segment curls radially away from the central axis, and the third segment curls radially toward the central axis.

5. The self-centering inferior vena cava filter of claim 3, wherein
    the third segment further comprises a fourth segment extending outwardly radially, the fourth segment is in a straight-line shape or a curved-line shape; and
    the fourth segment further comprises a fifth segment extending parallel to or curling toward the central axis.

6. The self-centering inferior vena cava filter of claim 2, wherein
    each of the plurality of struts of the filter members other than the filter member closest to the support portion comprises at least a first segment, a second segment, and a third segment extending sequentially outwardly radially from the center point of the filter member; and
    the first segment is in a straight-line shape and parallel to the central axis, the second segment is in a curved-line shape and curls outwardly radially, and the third segment is in a straight-line shape or a curved-line shape and extends gradually outwardly radially.

7. The self-centering inferior vena cava filter of claim 1, wherein
    the support portion comprises at least three support struts extending outwardly radially from the center point of the support portion and being symmetric about the central axis;
    an end of the support strut or a tangent of the end of the support strut, and the central axis define an angle therebetween, and the angle being less than or equal to 180 degrees; and
    a maximum outer diameter of the support portion is configured to be substantially coincident with an inner diameter of the blood vessel such that the support struts are configured to be supported on the blood vessel wall by point contact.

8. The self-centering inferior vena cava filter of claim 7, wherein
    each of the support struts comprises a first support segment and a second support segment extending sequentially outwardly radially from the center point of the support portion;
    the first support segment or a tangent of each point of the first support segment, and the central axis define an angle therebetween ranging from zero to 90 degrees;
    the second support segment or a tangent of each point of the second support segment, and the central axis define an angle therebetween greater than 90 degrees; and an end of the second support segment or a tangent of the end of the second support segment, and the central axis define an angle therebetween less than or equal to 180 degrees.

9. The self-centering inferior vena cava filter of claim 8, wherein the second support segment or a tangent of each point of the second support segment, and the first support segment define an angle greater than or equal to 90 degrees.

10. The self-centering inferior vena cava filter of claim 9, wherein
the second support segment comprises a first sub-segment, a second sub-segment, and a third sub-segment;
the radius of curvature of the second sub-segment is less than that of the first sub-segment; and
the second sub-segment and the central axis define an angle therebetween, the angle increasing along an extending direction of the second sub-segment.

11. The self-centering inferior vena cava filter of claim 9, wherein
the second support segment comprises a first sub-segment, a second sub-segment, and a third sub-segment; and
the second sub-segment is in a curved-line shape or a polyline shape with a C-shaped or V-shaped opening facing the central axis; each of the first sub-segment and the third sub-segment is in a straight-line shape or a fold-line shape, and the entire second support segment curls away from or toward the filter members.

12. The self-centering inferior vena cava filter of claim 8, wherein
the second support segment comprises a first sub-segment, a second sub-segment, and a third sub-segment;
the radius of curvature of the second sub-segment is less than that of the first sub-segment; and
the second sub-segment and the central axis define an angle therebetween, the angle increasing along an extending direction of the second sub-segment.

13. The self-centering inferior vena cava filter of claim 8, wherein
the second support segment comprises a first sub-segment, a second sub-segment, and a third sub-segment; and
the second sub-segment is in a curved-line shape or a polyline shape with a C-shaped or V-shaped opening facing the central axis; each of the first sub-segment and the third sub-segment is in a straight-line shape or a fold-line shape, and the entire second support segment curls away from or toward the filter members.

14. The self-centering inferior vena cava filter of claim 7, wherein
each of the support struts comprises a first support segment and a second support segment extending sequentially outwardly radially from the center point of the support portion; and
the second support segment or a tangent of each point of the second support segment, and the first support segment define an angle greater than or equal to 90 degrees.

15. The self-centering inferior vena cava filter of claim 7, wherein the cross-sectional area of each of the support struts of the support portion is gradually reduced toward the end of the support strut.

16. The self-centering inferior vena cava filter of claim 1, wherein
each of the at least two layers of the filter members comprises a plurality of struts, each of the plurality of struts of the filter member closest to the support portion has a first terminal away from the support portion;
each of the plurality of struts of the filter members other than the filter member closest to the support portion has a second terminal away from the support portion; and
a distance between the first terminal and the central axis is greater than a distance between any part of the support portion and the central axis and less than a distance between the second terminal and the central axis.

17. A self-centering inferior vena cava filter, comprising:
a filter portion configured to filter thrombi, comprising at least two layers of filter members extending along a central axis of the self-centering inferior vena cava filter, the at least two layers of filter members being adjacent to each other and staggered around the central axis;
a support portion configured to prevent the self-centering inferior vena cava filter from tilting, extending outwardly radially from a center point of the support portion in a direction towards the filter portion and then curling inwardly radially in a direction away from the filter portion, and configured to be supported on a blood vessel wall by point contact; and
a retrieval portion connected with both the filter portion and the support portion;
wherein
the support portion comprises support struts,
for each of the support struts, a free end of the support strut extends from an apex of the support strut inwardly radially towards the filter portion, and
the apex is farther away from a free end of the filter portion than the free end of the support strut in a direction parallel to the central axis.

18. The self-centering inferior vena cava filter of claim 17, wherein
each of the at least two layers of the filter members comprises a plurality of struts extending outwardly radially from a center point of the filter members, the plurality of struts of the filter members adjacent to each other being staggered around the central axis, and the plurality of struts of the filter member closest to the support portion being staggered with the support struts of the support portion.

19. The self-centering inferior vena cava filter of claim 17, wherein
the support portion comprises at least three support struts extending outwardly radially from the center point of the support portion and being symmetric about the central axis;
an end of the support strut or a tangent of the end of the support strut, and the central axis define an angle therebetween, and the angle being less than or equal to 180 degrees;
a maximum outer diameter of the support portion is configured to be substantially coincident with an inner diameter of the blood vessel such that the support struts are configured to be supported on the blood vessel wall by point contact; and
the end of the support strut extends, in a direction close to the central axis of the self-centering inferior vena cava filter, inwardly radially relative to a portion of the support strut where the support portion has the maximum outer diameter.

20. The self-centering inferior vena cava filter of claim 17, wherein each of the at least two layers of the filter members comprises a plurality of struts, each of the plurality of struts of the filter member closest to the support portion has a first terminal away from the support portion;
each of the plurality of struts of the filter members other than the filter member closest to the support portion has a second terminal away from the support portion; and
a distance between the first terminal and the central axis is greater than a distance between any part of the support portion and the central axis and less than a distance between the second terminal and the central axis.

* * * * *